United States Patent [19]
Gatto

[11] Patent Number: 6,059,776
[45] Date of Patent: May 9, 2000

[54] ELECTROSURGICAL LASER SHEARS

[76] Inventor: Dom L. Gatto, 36 Flat Rock Rd., Branford, Conn. 06405

[21] Appl. No.: 08/935,818

[22] Filed: Sep. 23, 1997

[51] Int. Cl.[7] .................................................. A61B 17/36
[52] U.S. Cl. .................................. 606/13; 606/16; 607/89
[58] Field of Search .................................. 606/15–17, 45, 606/49–52

[56] References Cited

U.S. PATENT DOCUMENTS

| | | | |
|---|---|---|---|
| 1,754,806 | 4/1930 | Stevenson | 128/318 |
| 4,499,899 | 2/1985 | Lyons, III | 128/305 |
| 5,147,356 | 9/1992 | Bhatta | 606/37 |
| 5,209,747 | 5/1993 | Knoepfler | 606/16 |
| 5,342,358 | 8/1994 | Daikuzono | 606/45 |
| 5,389,104 | 2/1995 | Hahnen et al. | 606/174 |
| 5,395,375 | 3/1995 | Turkel et al. | 606/83 |
| 5,395,386 | 3/1995 | Slater | 606/170 |
| 5,423,804 | 6/1995 | Kulick | 606/14 |
| 5,431,674 | 7/1995 | Basile et al. | 606/170 |
| 5,611,796 | 3/1997 | Kamami | 606/15 |

Primary Examiner—Lee Cohen
Assistant Examiner—Roy Gibson
Attorney, Agent, or Firm—John S. Hale; Gipple & Hale

[57] ABSTRACT

A combined mechanical cutter and laser function surgical instrument, constructed with; a handle housing and a disposable tip assembly removably mounted to the handle housing. The disposable tip assembly has a hollow tube with a proximal and a distal end, a stationary jaw mounted to the distal end of the hollow tube, a movable jaw which pivots relative to the stationary jaw and a actuating mechanism coupled to the movable jaw for moving the movable jaw, the actuating mechanism being driven from linkage in the handle housing mounted to the proximal end of the hollow tube. Quick disconnects are mounted on the proximate end of the hollow tube to engage the handle housing and a laser energy conductive optic fiber extends through the hollow tube and mounted to the stationary jaw. A laser energy dispensing tip member is mounted on and insulated from the stationary jaw and is connected to the optic fiber to transport laser energy from a remote laser energy generator.

10 Claims, 8 Drawing Sheets

ELECTROSURGICAL LASER SHEARS

FIELD OF THE INVENTION

The present invention generally relates to the field of tissue removal, cauterization and ablation and more specifically relates to a device having a reusable or resposable shear handle housing and a detachable, disposable cutting tip which tip incorporates a mechanical cutting device and either a laser or electrosurgical device or both for tissue removal, cauterization and ablation to facilitate surgical tissue removal during ENT or other surgical procedures.

BACKGROUND OF THE INVENTION

Generally in the field of surgery, mechanical cutters utilizing a reciprocal or rotating cutting element have been used to sever tissue of a patient. Cutting devices that use light energy to cut tissue are also well known in the art. Electrosurgical devices for tissue excision or cauterization similarly have a long medical history. Such instruments have encountered numerous problems due to their one dimensional capabilities and have failed to meet many of the needs of a surgeon performing a surgical procedure. Thus, there is a requirement of a multiplicity of instruments which have to be sterilized after each procedure representing a significant cost as well as instrument down time and shortened instrument life span due to sterilization. The following patents constitute representative types of prior art instrumentation directed toward tissue removal.

U.S. Pat. No. 5,389,104 issued to Hahnen et al. discloses an arhroscopic surgical instrument which includes a hollow tube with an actuator coupled to its proximal end and an end effector coupled to its distal end. The actuator and the end effector are coupled by a cylindrical push rod that passes through the hollow tube. The push rod includes a frangible link in the form of a flattened portion with strength reducing semicircular side cuts which break when a predetermined force is applied to the end effector by the actuator. The end effector includes a stationary jaw and a movable jaw. An electrical connector is provided to the insulated hollow tube for supplying the jaws with a cautery current.

U.S. Pat. No. 4,499,899 to Lyons, III discloses a fiber-optic illuminated microsurgical scissors device. The rotary cutting scissors device incorporates an internal fiber-optic light source which constantly illuminates the line of cut by moving in tandem with the instrument during surgery.

Numerous mechanical cutters are described in the prior art. An example of a surgical mechanical cutting instrument is disclosed in U.S. Pat. No. 1,754,806 to Stevenson which is directed towards an instrument for operations on thin osseous tissue. Another surgical mechanical cutting instrument in the form of a disposable arthroscopic surgical instrument is described in U.S. Pat. No. 5,395,375 to Trukel et al. An endoscopic pericardial scissors is disclosed in U.S. Pat. No. 5,395,386 issued to Slater and another mechanical cutter in the form of a compound motion cutting device is set forth in U.S. Pat. No. 5,431,674 to Basile et al.

There currently exists a need for a device capable of providing the surgeon with a disposable sharp, sterile mechanical reciprocating or scissors blade cutting tip which simultaneously makes available to the surgeon the ability to quickly and conveniently cauterize tissue and/or excise tissue in situations in which reciprocating or rotating blade mechanisms are not preferred or are contraindicated. Present blade mechanisms have a life span ranging from 10 to 15 operations before the cutting blades become to dull or nicked to use. Traditionally the instruments are then thrown away or sent back to the manufacturers for refabrication. The present inventive device meets this need by providing the surgeon with a reusable or resposable shear housing which includes at least one throughgoing bore for a laser transmission cable and/or an electrosurgical wave form transmission cable. A disposable tip which is quickly attachable to and removable from the shear handle housing incorporates a mechanical reciprocating blade cutting mechanism and a laser delivery tip and/or an electrosurgical tip.

Although electrosurgical devices can be used to sever tissue, they cause damage and neurosis to surrounding tissues. Lasers and mechanical cutters provide the surgeon with a superior method of cutting tissue but a need to coagulate the tissue and blood vessels still exists. The mechanical cutter of this invention has a plurality of cutting means disposed at the distal end of a long disposable shaft. This design is frequently used in surgical procedures performed within the body through small openings in the body. The bleeding that normally accompanies any type of invasive surgery obstructs the surgeon's view and slows the procedure. Therefore, it is desirable to achieve hemostasis at the surgical site as quickly as possible to avoid prolonging the surgical procedure. The present invention allows this by providing the surgeon with a readily accessible means of stopping bleeding after an incision has been made. The surgeon need not stop the surgical procedure to reach for a second instrument to coagulate the tissue at the surgical site. In addition to the above-mentioned electrosurgical coagulation and cutting, the present invention affords the surgeon the opportunity to coagulate or incise tissue using a laser.

While some lasers are effective coagulators and cutters, certain other types of lasers, $CO_2$ lasers for example, are effective at cutting tissue but are not good coagulators. It is desirable when using such devices to have a means for stopping bleeding because blood loss weakens the patient and obstructs the surgeon's view. Using separate hand pieces for cauterizing and cutting is, as previously mentioned, unwieldy and needlessly prolongs the procedure to the detriment of the patient. There are also situations in which the surgeon would like to use a mechanical cutter and a laser coagulator. Certain lasers are good coagulators but are poor tissue cutters. The YAG laser, for example, is sometimes used as a coagulator but is not considered to be a good tissue cutter. Similarly, a plurality of different types of electrosurgical coagulators are needed by surgeons depending on the type of surgery being performed. Monopolar, bipolar and resistive electrosurgical devices are capable of coagulating blood. All three types are included within the scope of this invention because they each serve different purposes. A heated implement can provide effective hemostasis only if small blood vessels have been severed, but if larger vessels are involved, a high frequency electrical current is preferred.

The mechanical cutting of the tissue at the surgical site is preferably performed by a pivoting cutter blade which attached to the distal end of the disposable tip. The lumen of this disposable tip can be used to provide a path or passageway from the housing to the distal end of the device for an optical fiber, electrical conductor strand, and if desired suction.

SUMMARY OF THE INVENTION

The inventive electrosurgical laser shears hand piece of the present invention is comprised of a reusable, resposable, lightweight shear housing assembly which is provided with a quick disconnect mechanism to receive a disposable tip which includes a mechanical cutter and either a laser cutter/ coagulator or an electrosurgical cutter/coagulator device or both. The disposable tip assembly for use with the shear housing handle is provided to the surgeon in a sterile, sealed package for immediate use in surgery and is disposed of after surgery. Alternately, the disposable tip assembly can be separately sterilized for sequential usage. The disposable tip includes a surgical blade pivotally attached to a pin member that is secured to a tubular shaft near the distal end thereof. The blade is partially enclosed in an outer tip member and is actuated, or pivoted, by an actuator that is slidably disposed within the tubular shaft. The actuator is coupled to the blade through an actuator link. A locking hub on the proximal end of the disposable tip and a rotator member and an actuator shaft lock bushing cooperate too removably secure the disposable tip to the shear housing. A rotator lock member pivotally attached on an underside of the shear housing is provided to facilitate the quick removal of the disposable tip. A thumb loop member pivotally attached to the proximal end of the shear housing slides an action plunger slidably disposed within the shear housing which in turn reciprocates the actuator shaft lock bushing to control the movement of the blade member.

The shear housing and disposable tip can also cooperate to provide laser transmission means to deliver light energy to the surgical site through an optical fiber connected to a remote laser source. The reusable or resposable housing and the disposable tip incorporate, a flexible laser fiber which has a quick connect mechanism for rapid attachment to a surgical laser source. The surgical laser source is typically located in a housing remote from the surgical site.

An electrosurgical system usually includes a radio frequency generator, an electrode and a cathode. The electrode in this invention is located in at the distal end of the disposable tip of the hand piece. An electrosurgery radio frequency (R.F.) generator used with the electrosurgical portion of the inventive device, can be housed in a separate unit or it can be incorporated in the same unit with the laser generator. The high-frequency electrical current created by the R.F. generator flows from the electrode on the distal end of the disposable tip through the surgical site; the current then returns to the generator from the patient, typically through a dispersive cathode and a cable attached thereto, back to the generator. The large area covered by the cathode prevents burns to the patient by creating a low current density contact with the patient in contrast to that created by the electrode. The high current density at the surgical site heats the tissue adjacent to the electrode to a degree sufficient to cause hemostasis, create an incision or both.

Any of the embodiments of the electrosurgical laser shears of this invention can include a cautery device which can be either a laser cautery device, an electrocautery device or any other type of cautery device known in the art. The laser cautery device can use the same optical fiber as the laser cutting means or it can use a separate optical fiber.

An object of this invention is to provide the surgeon with a single surgical hand piece which provides mechanical, laser, and electrocautery or laser cautery power in a single hand piece to enable the surgeon to cut tissue mechanically or with a laser and then cauterize the wound with a laser or an electrocautery device.

It is a further object of this invention to provide the surgeon with a resposable shear housing with replaceable disposable tips of various configurations so that the surgeon can choose which tip configuration he or she needs based on the requirements of the surgical procedure and can quickly attach the appropriate tip to the resposable hand piece housing and discard the chosen tip after the procedure is completed.

It is yet another object of this invention to provide the surgeon with a plurality of disposable tips for a reusable or resposable shear housing which can provide the surgeon with a new tip for each surgical procedure so that the mechanical cutter is always first-use sharp and the tip is always sterile.

It is still another object of the invention to provide the surgeon with a low cost, disposable surgical cutting implement which can be used once in one surgical procedure and then discarded under standard medical disposal procedures.

Another object of the invention is to provide the surgeon with a streamlined hand piece which is easy to use, reduces hand fatigue and accommodates a wide range of cutting techniques.

Another object of the present invention is to provide the user with a surgical hand piece which requires only very simple assembly and disassembly with no cleaning and no sterilizing of the cutting mechanism.

It is also an object of the present invention to provide the surgeon with a device which contains no electronics in the hand piece so there is no danger of electrical shock to the patient or the surgeon; the electronics being completely isolated from the shears housing.

Still another object of this invention is to provide the surgeon with a new disposable cutter for each patient to reduce the possibility of cross contamination between patients.

In the accompanying drawings, there is shown an illustrative embodiment of the invention from which these and other objectives, novel features, and advantages will be readily apparent.

DETAILED DESCRIPTION OF THE INVENTION

The preferred embodiment and the best mode of the invention is shown in FIGS. 1 through 4 and 9 through 39.

Figure 1:
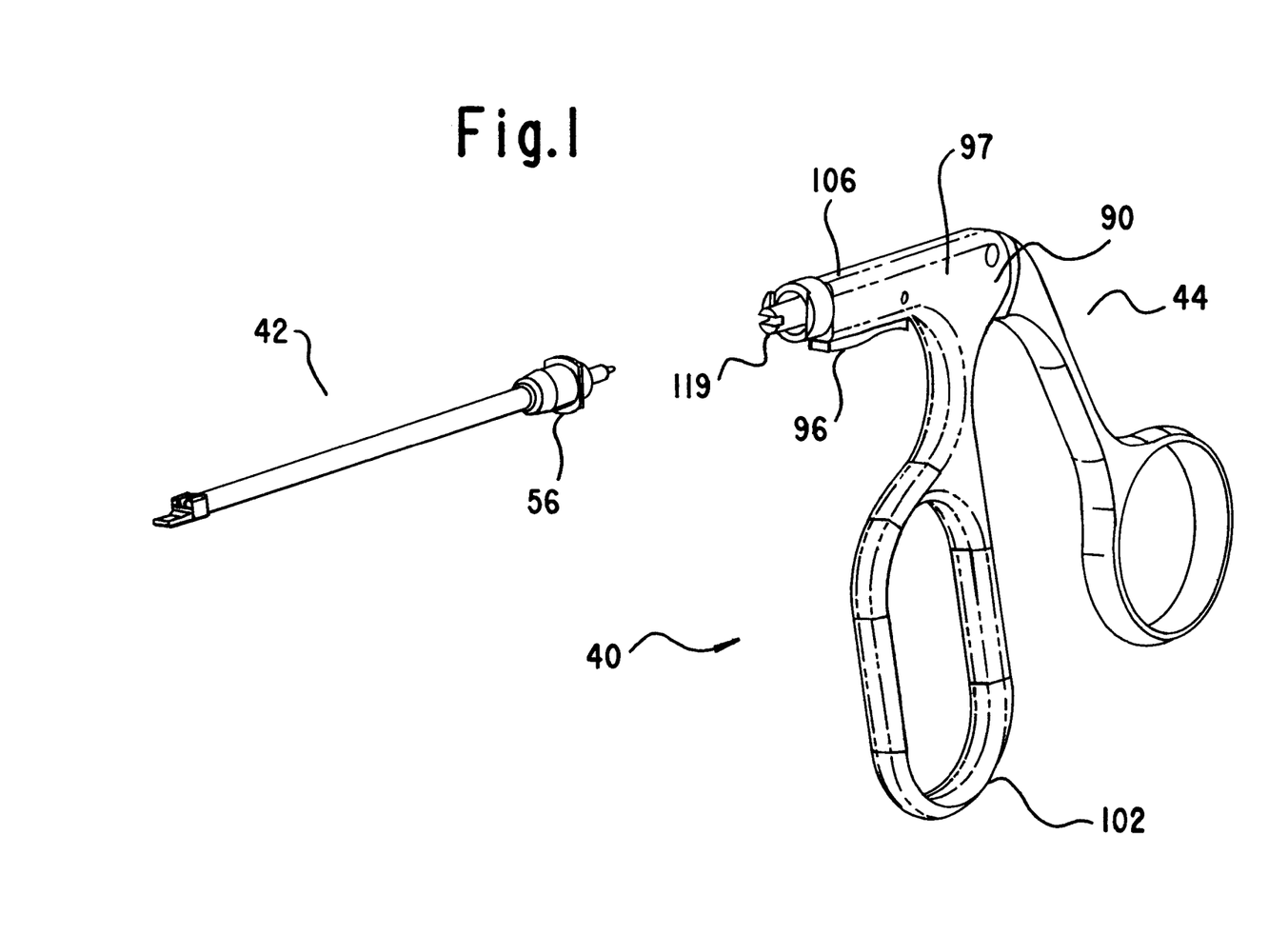
FIG. 1 is an exploded perspective view of an electrosurgical laser shears apparatus invention taken from the front showing the shear handle housing and a disposable tip.
Figure 2:
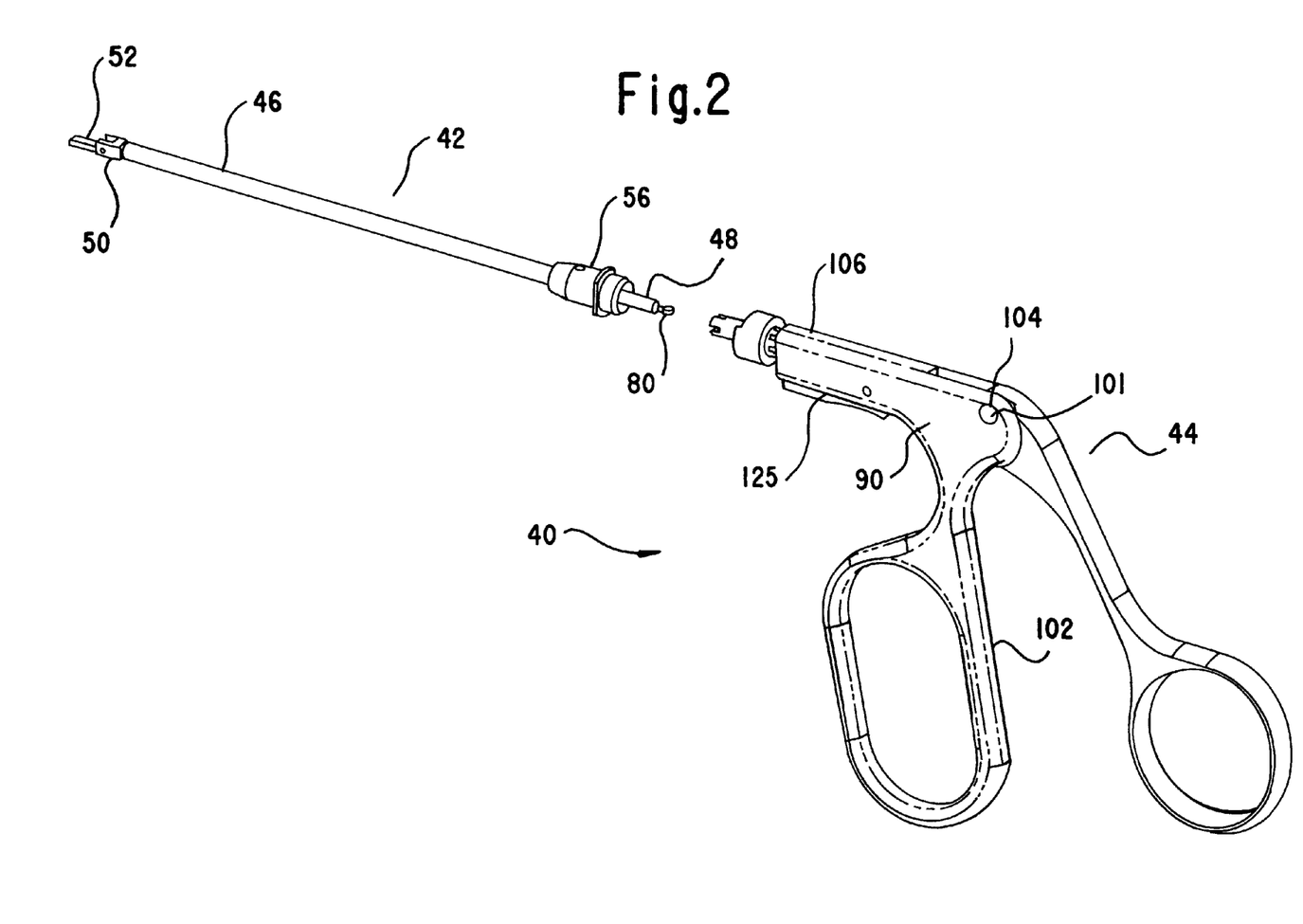
FIG. 2 is an exploded perspective view of an electrosurgical laser shears apparatus invention shown in FIG. 1 taken from the side rear showing the shear handle housing and a disposable tip.
Figure 3:
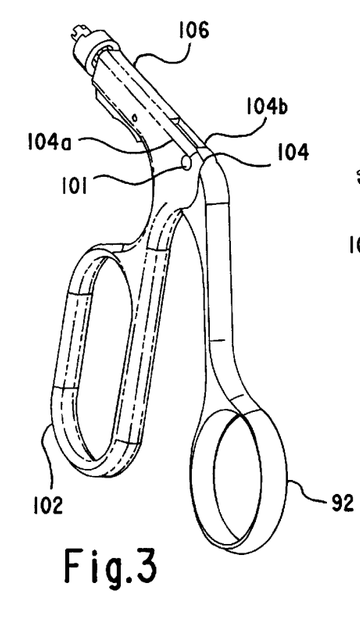
FIG. 3 is a rear perspective view of shear handle housing of the electrosurgical shears apparatus invention shown in FIG. 1.
Figure 4:
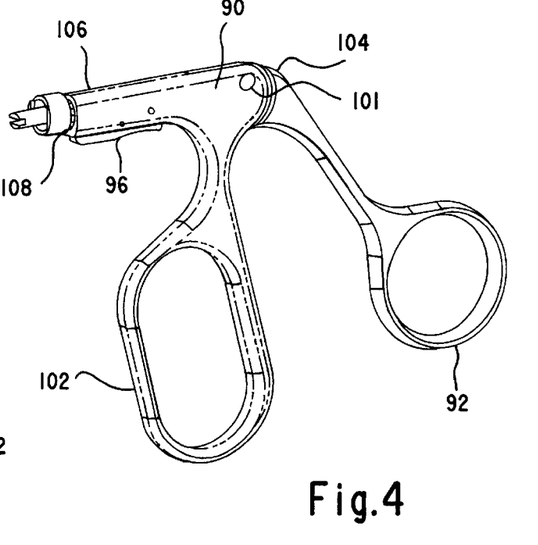
FIG. 4 is a side perspective view of the shear handle housing of the electrosurgical shear apparatus invention shown in FIG. 1.
Figure 5:
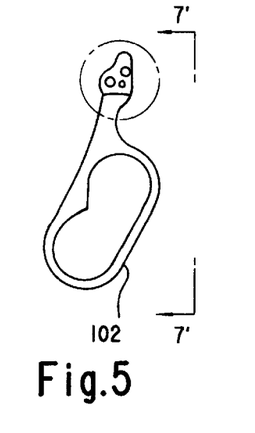
FIG. 5 is a side elevational view of a alternate embodiment of a finger loop member of the electrosurgical shears apparatus invention where the finger loop member is moveable.
Figure 6:
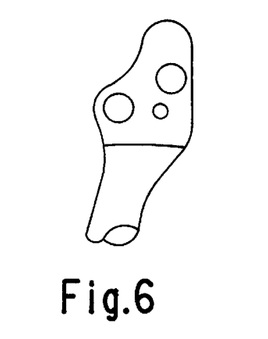
FIG. 6 is an enlarged view of the circled portion of finger loop member of FIG. 5.
Figure 7:
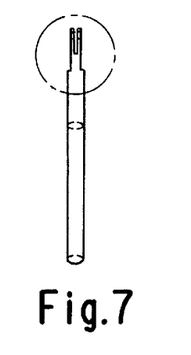
FIG. 7 is an end elevational view taken along line 7'—7' of the finger loop member shown in FIG. 5.
Figure 8:
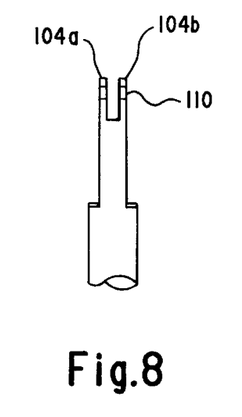
FIG. 8 is an enlarged view of the circled portion of the finger loop member shown in FIG. 7.
Figure 9:
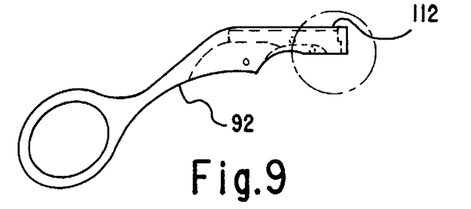
FIG. 9 is a side elevational view of the thumb loop member of the electrosurgical shears apparatus invention.
Figure 10:
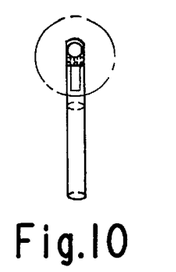
FIG. 10 is an end elevational view of the thumb loop member shown in FIG. 9.
Figure 11:
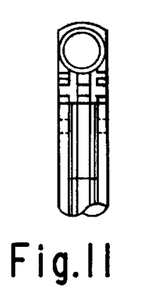
FIG. 11 is an enlarged end portion of the thumb loop member shown in the circle of FIG. 10.
Figure 12:
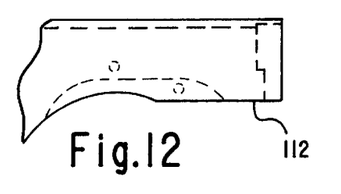
FIG. 12 is an enlarged end portion of the thumb loop member shown in the circle of FIG. 10.

FIGS. 1 and 2 shows an exploded view of an electrosurgical laser shear assembly 40, including a disposable tip assembly 42, and a shearing handle housing 44.

Figure 35:
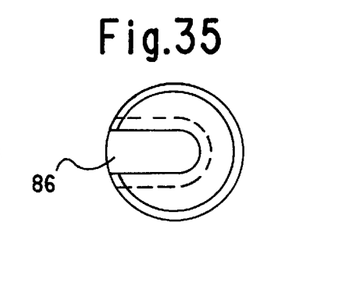
FIG. 35 is an end view taken along line 35'—35' of the actuation link member shown in FIG. 34.
Figure 36:
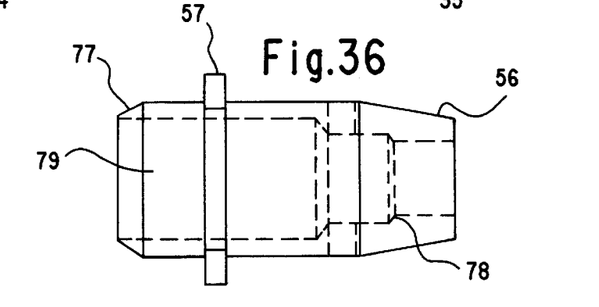
FIG. 36 is a side elevational view of a locking hub member of the disposable tip assembly.
Figure 37:
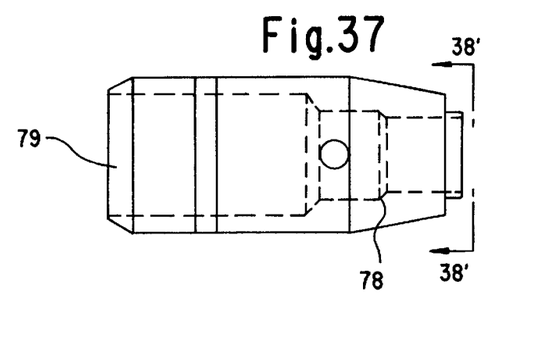
FIG. 37 is a top plan view of the locking hub member shown in FIG. 36.
Figure 38:
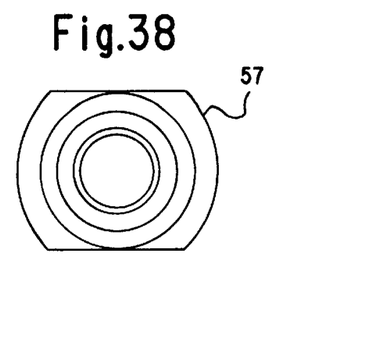
FIG. 38 is an end view taken along line 38'—38' of the locking hub member shown in FIG. 37.

The disposable tip assembly 42 is comprised of a tubular shaft member 46 (FIGS. 25, 26), an actuator member 48 (FIGS. 27, 28), an outer tip member 50 (FIGS. 29, 30), an inner tip member 52 (FIGS. 31,32), an actuation linkage member 54 (FIGS. 33–35), and a locking hub 56 (FIGS. 36–38).

Figures 25, 26:
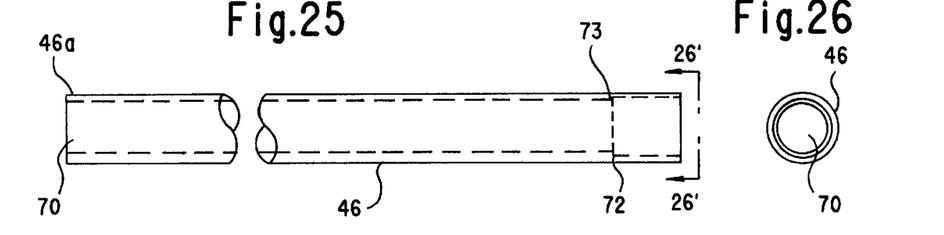
FIG. 25 is a side elevational view of a tubular shaft member of the disposable tip assembly.
FIG. 26 is an end view taken along line 26'—26' of the tubular shaft member shown in FIG. 25.
Figure 27:
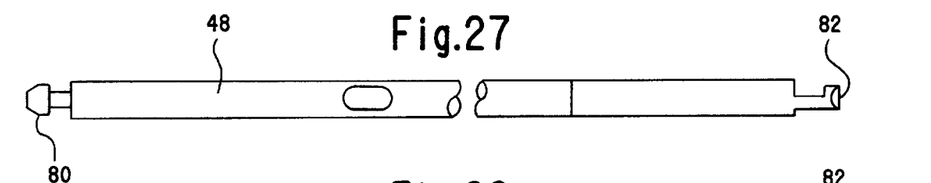
FIG. 27 is a side elevational view of an actuator member of the disposable tip assembly.
Figure 28:
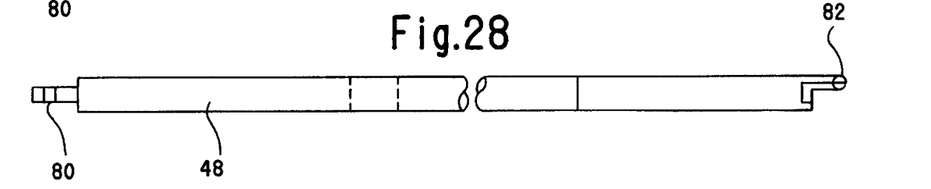
FIG. 28 is a top plan view of the actuator member shown in FIG. 27.

The tubular shaft 46 defines a throughgoing bore 70 which has a stepped enlarged recessed end portion 72 at its distal end to receive and securely hold the annular male portion 62 of the outer tip member to secure the outer cutting tip member 50 in the tubular shaft 46.

Figure 29:
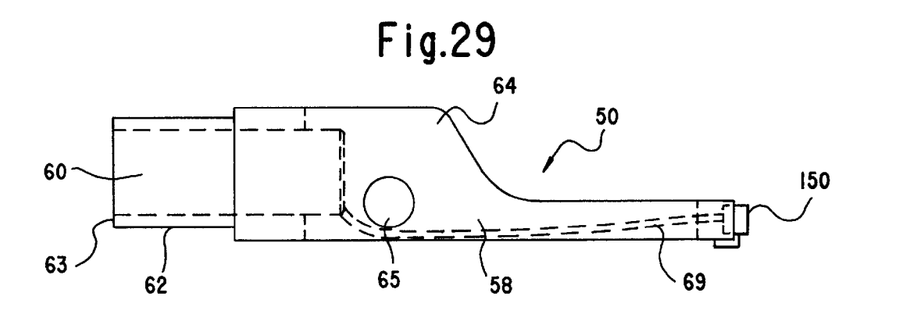
FIG. 29 is an enlarged side elevational view of the spear outer tip member of the disposable tip assembly.
Figure 30:
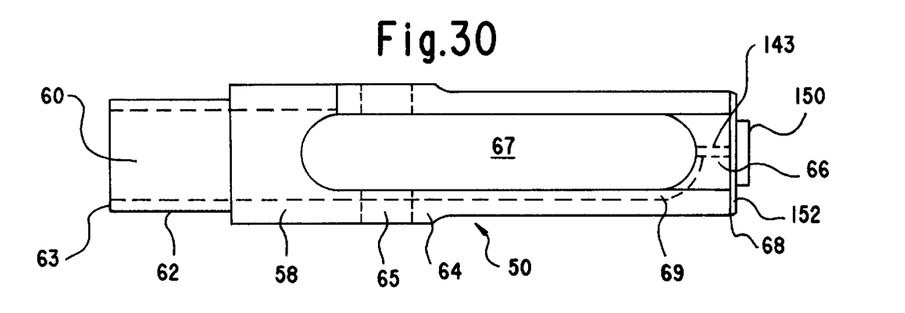
FIG. 30 is an enlarged top plan view of the shear outer tip member shown in FIG. 29.

The outer cutting tip member 50 which is mounted to tubular shaft member 46 is comprised of an outer tip housing 58 defining a throughgoing tip bore 60. The recessed annular male portion 62 is integrally formed on the proximal end of the outer cutting tip housing 58 with its end 63 being adapted to abut against internal shoulder 73 of tubular shaft 46. Outer tip side walls 64 extend from the outer tip housing 58 and define a plurality of outer tip apertures 65 and in connection with cross support 66 define slot 67 to form an outer tip blade bracket. An insulating member 152 is mounted to the distal end 68 by adhesive or a suitable securing means and a cutter and/or cogulator tip member 150 is mounted onto the insulating member and connected to an optical fiber 144 or insulated electrical conductor cable 162 mounted in channel 69.

Figure 31:
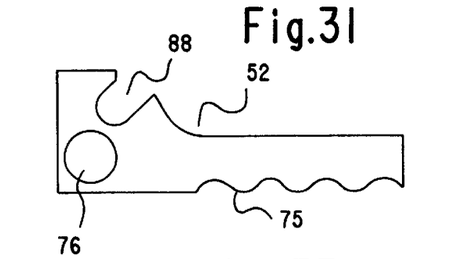
FIG. 31 is a side elevational view of a shear inner tip member of the disposable tip assembly.
Figure 32:
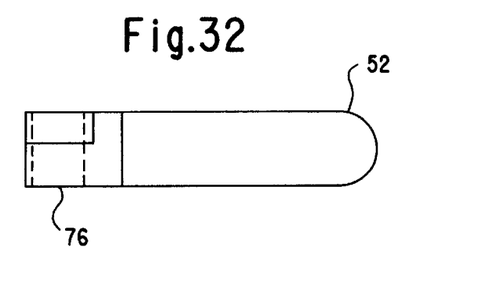
FIG. 32 is a top plan view of the shear inner tip member shown in FIG. 31.
Figure 33:
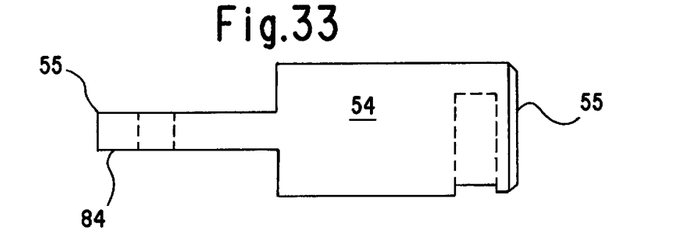
FIG. 33 is a side elevational view of an actuation link member of the disposable tip assembly.
Figure 34:
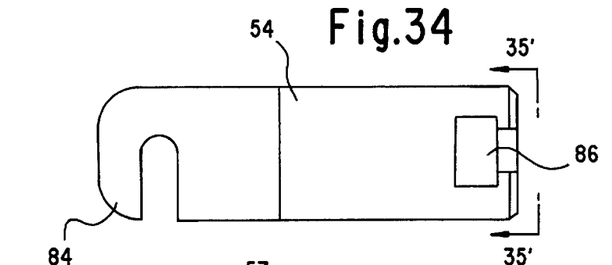
FIG. 34 is a top plan view of the actuation link member shown in FIG. 33.

The inner cutting tip member 52 defines an inner tip aperture 76 that is aligned with the plurality of outer tip apertures 65 to cooperate to form a passage for a blade pin 78 to hold the inner tip member 52 in pivotal engagement within the outer tip bracket 68. A lower portion of the inner tip member defines cutting blade 75.

The locking hub 56 includes a distal stepped bore 78 that receives and securely holds the external surface of proximal end 46a of the tubular shaft 46. The larger adjacent coaxially aligned bore 79 receives and holds the distal split end 118 of bushing member 98. The actuator member 48 is slidably disposed within bore 70 of the tubular shaft 46 so that a spatulated tip portion 80 of the actuator member 48 extends out of the proximal end of the tubular shaft 46 through locking hub 56. The distal end of the actuator member 48 defines an actuator hook 82 which engages the actuation link member 54 via a link hook 84 defined at the proximal end 55 of the actuation link member 54. The actuation link member 54 defines at its distal end 53 a transverse cutout 86 as best seen in FIG. 35 that engages an angled blind and arcuate slot 88 on the inner cutter tip member 52 so that reciprocation of the actuator member 48 causes pivoting of the inner cutter tip member 52.

The shear handle housing 44 is constructed of a main body 90, with an integrally formed finger loop portion 102, a thumb loop member 92, a rotator member 94, a rotator lock member 96, an actuator shaft lock bushing member 98, and an actuation plunger member 100. The main body 90 is formed with a yoked proximal portion 104 and an elongated distal portion 106. A main body bore 97 extends from the yoked portion 104 through the elongated distal portion 106 and terminates at the distal end in a distal bore opening 108. The yoked proximal portion 104 of the shear handle housing 44 is formed with two identical spaced yoke arms 104a and 104b, each of which defines a throughgoing aperture 110, the aperture 110 being aligned to receive a pin member 101. The same structure is utilized on the finger loop member when it rotated and the thumb loop member is integrally formed with the main body. The thumb loop member 92 is pivotally supported by the pin member 101 so that a thumb loop extension 112 integrally formed with the thumb loop member 92 is slidably disposed within the main body bore 97.

Figures 16, 17:
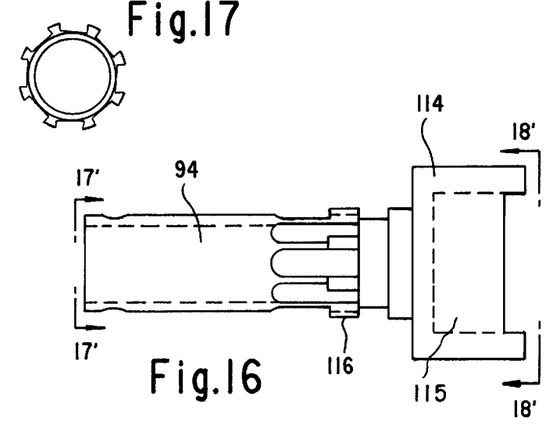
FIG. 16 is a side elevation view of a rotator member of the electrosurgical shears apparatus invention.
FIG. 17 is an end view of the rotator member taken along line 17'—17' of FIG. 16.
Figure 18:
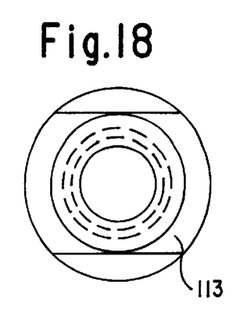
FIG. 18 is an end view of the rotator member taken along line 18'—18' of FIG. 16.
Figure 19:
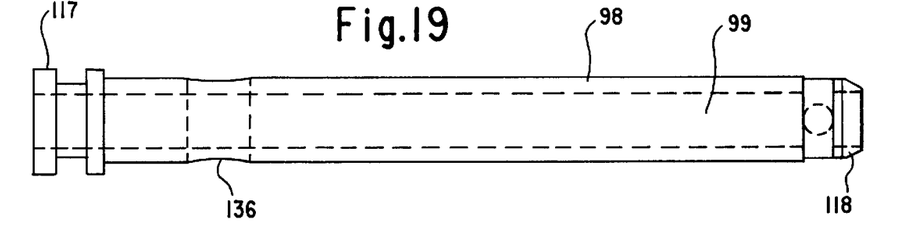
FIG. 19 is a side elevational view of the actuator shaft lock bushing member of the electrosurgical shears apparatus invention.
Figures 20, 21:
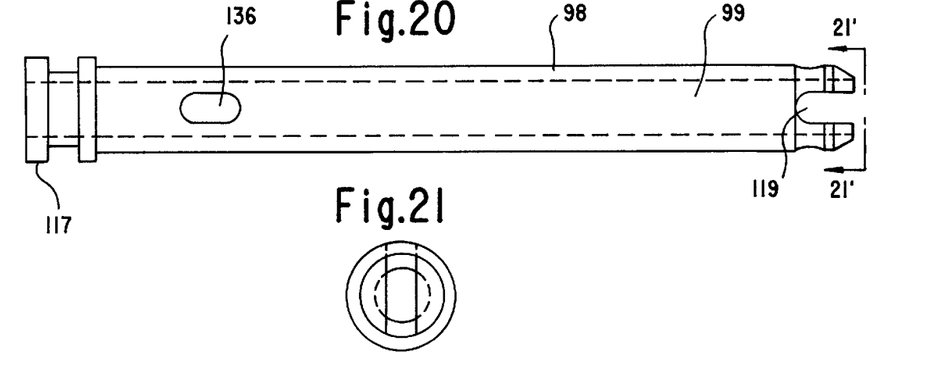
FIG. 20 is a top plan view of the actuator shaft lock bushing member shown in FIG. 19.
FIG. 21 is an end view taken along line 21'—21' of the actuator shaft lock bushing member shown in FIG. 20.

A proximal end of the rotator member 94 is mounted in the distal end of the bore 97. The rotator member defines an annular hub receptor 114 which is held on a portion of a tubular body structure 116 of the rotator member 94 which extends out of the distal bore opening. Recess 115 is configured in the hub receptor to receive the end 77 of the locking hub and flange 57 of the locking hub orients and seats the locking hub into cutout area 113 of the hub receptor 114.

Figure 22:
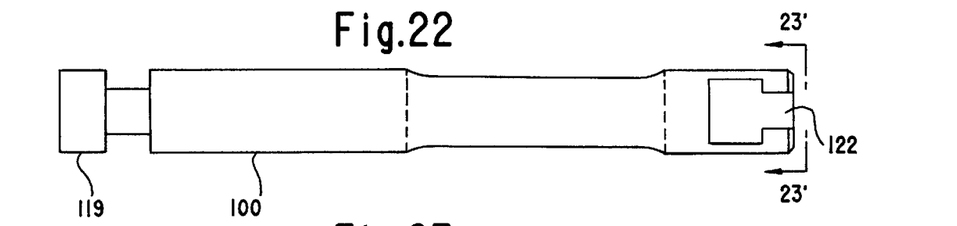
FIG. 22 is a side elevational view of the actuation plunger member of the electrosurgical shears apparatus invention.
Figure 23:
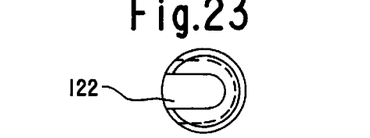
FIG. 23 is an end view taken along line 23'—23' of the actuation plunger member shown in FIG. 22.
Figure 24:
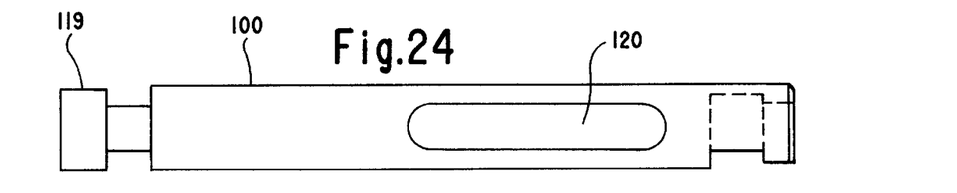
FIG. 24 is a top plan view of the actuation plunger member shown in FIG. 22.

A actuator shaft lock bushing member 98 (FIGS. 19–21) defines a throughgoing bore 99, a double collar end 117 at the proximal end and a split end 118 formed by an arcuate cutout 119 at a distal end. The bushing member 98 is disposed within the shear handle housing bore 97 so that the split end 118 extends through the rotator member 94 to a region outside the main body portion 90 of the shears housing 44 to receive the proximal end of the actuator member 48. The actuation plunger member 100 shown in FIGS. 22–24 is slidably mounted in throughoing bore 99 and defines a base piston shaped end section 119 at the proximal end, an oval lock port 120 and arcuate stepped slot 122 at its distal end. The stepped slot 122 receives the spatulated tip portion 80 of the actuator member 48.

Figure 13:
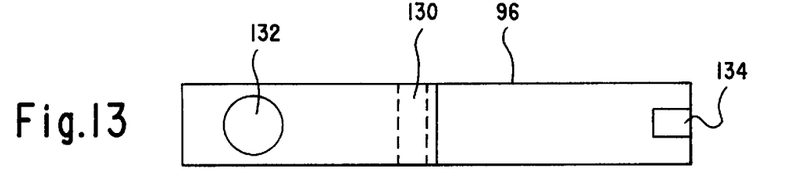
FIG. 13 is a top plan view of the rotor lock member of the electrosurgical shears apparatus invention.
Figure 14:
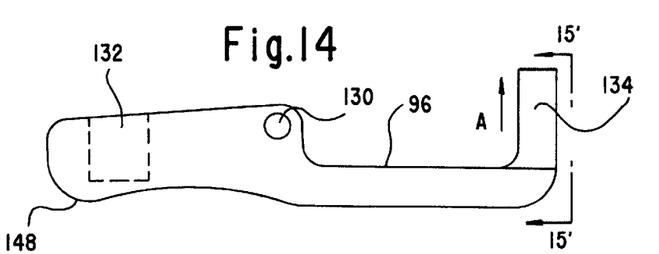
FIG. 14 is a side elevation view of the rotor lock member of FIG. 13.
Figure 15:
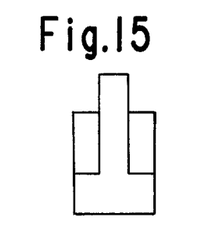
FIG. 15 is an end elevation view of the rotor lock member of FIG. 14 taken along 15'—15'.

A rotator lock member 96 is pivotally connected to a bottom side of the main body portion 90 of the shear housing 44 to release or lock the disposable tip assembly 42 in place within the bore 97. The rotator lock member 96 is pivotally attached to the shear housing 44 through a rotator lock pin 125 that extends through a plurality of aligned housing lock apertures and an aligned rotator lock pivot aperture 130. The rotator lock member 96 defines a blind spring bore 132 that receives a lock spring (not shown in the figures), but preferably a standard coil spring, to pivotally bias a locking rod 134 in direction as shown in FIG. 13. The locking rod 134 is integrally formed on the rotator lock member 96 and traversely extends away from the rotator lock body into a transverse lumen (not shown) in the shear housing 44.

In the assembled configuration of the electrosurgical laser shears assembly 40, the actuator shaft locking bushing member 98 is slidably positioned within the shear handle housing bore 97 and the actuation plunger member 100 is slidably disposed within bore 99 of the actuator shaft locking bushing member 98. The locking rod 134 passes through a bushing locking port 136 and the aligned oval lock port 120 on the actuation plunger. Thus, when the electrosurgical laser shear assembly 40 is in assembled form, the locking rod 134 prevents the actuator shaft locking bushing member 98 from sliding or rotating in the bore 97, but allows limited axial movement of the actuation plunger member 100 within bore 99 of the shaft locking bushing member 98. This will be described later when the operation of the assembly 40 is discussed.

Figure 39:
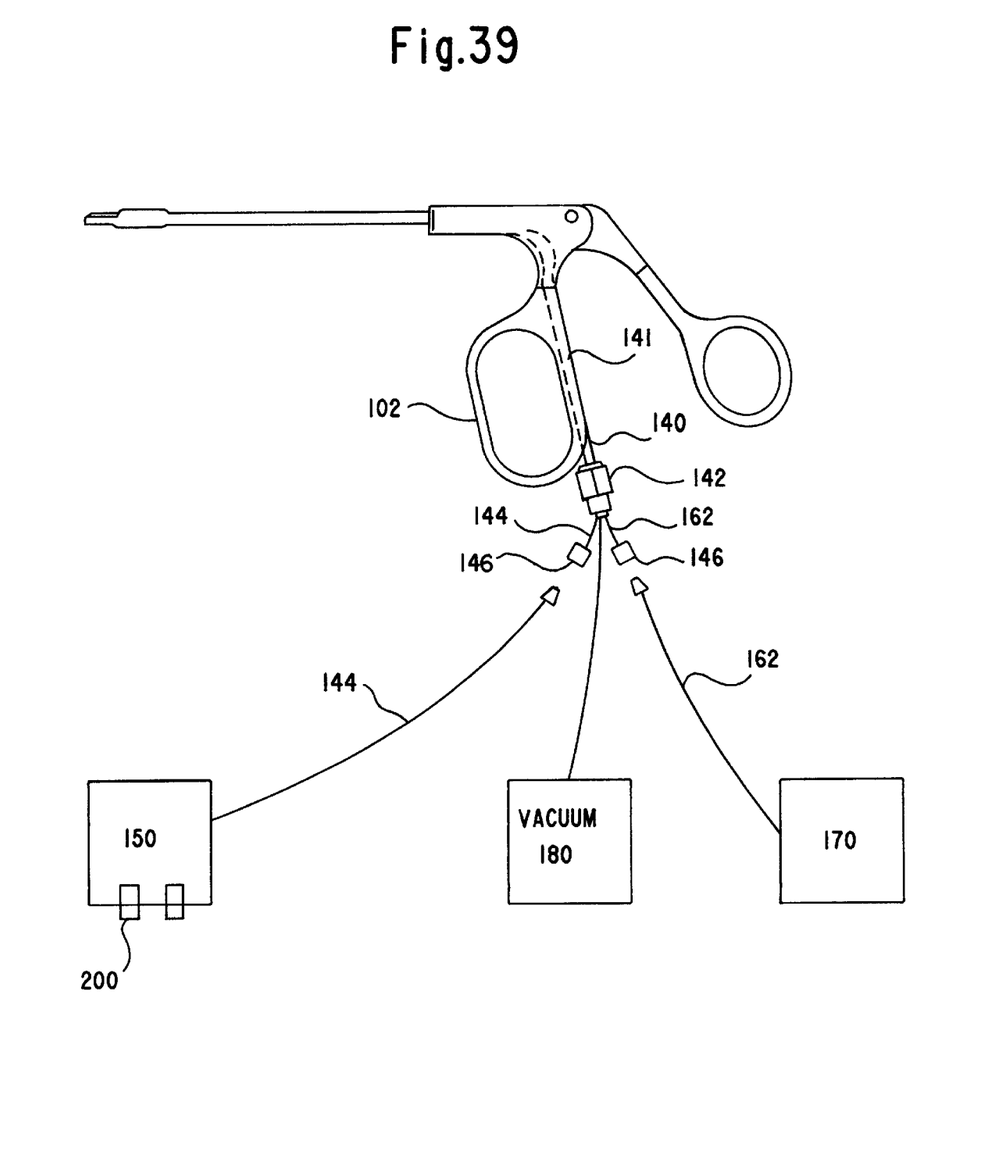
FIG. 39 is a schematic representation of the electrosurgical shears invention.

The shear assembly can include either a laser fiber 144, an electrosurgical conductor cable 162 or both. When the laser fiber is included, the finger loop 102 on the shear housing 44 includes a connection tube member, generally designated 140, leading into channel 141 and includes a lumen connector member 142 to facilitate connection and passage of a laser fiber from an exterior remote source as is shown in FIG. 39. A disposable laser fiber is provided to the surgeon in a length long enough to isolate the laser source from the surgical area. The laser fiber 144 has a quick connect coupler 146 at a proximal end thereof for connection to the light energy generator 150 and is covered along the majority of its length by a laser fiber sheath. Alternately, the proximal end of the laser fiber has a length of exposed fiber optic cable which extends out of the proximal end of the sheath for insertion into the lumen or channel 141 so the fiber can be prethreaded through the passage in the shears housing 44 and an aligned passage in the disposable tip 42 in contact with tip member 150 to transport surgical laser light energy to a surgical site. The sources of laser light energy which are transported by the fiber optic strands are controlled by a plurality of foot pedals 200 pivotally disposed on a pedal housing light energy generator that can be placed on the floor beside the physician. One of the foot pedals can control the laser by toggling the laser light on and off, and the other pedal can select which laser light source within the remote laser source housing will be activated at a particular time.

When a laser light transmission means is included in the shear assembly 44, which is the preferred usage, the laser fiber passes through the tubular shaft member 46 and out an axially aligned end aperture 143 formed in the transverse cross member 66 of the outer tip bracket 66 to laser tip member 150. In this configuration, the laser fiber passes alongside of and parallel to the inner cutting tip 52 at the distal end of the disposable tip 42 to transmit the laser energy out the distal end of the outer tip member 50 via the contact laser tip 150 to the surgical site. Suitable laser tips which an be used as the laser tip member with the invention are manufactured by Surgical Laser Technology, Inc. and are commercially available. Such tips are commercially identified as Scalpel –9 mm (GRP-2, GRP4, GRP-6, GRP-8); Scalpel –19 mm (ERP-2, ERP-4, ERP-6), Round Probe (MIR 1.5, MIR 3.5, MTRL 3), Large Round Probe MIRL6, MIRL7), Chisel Probe (MD2.5, MD 3.5), Large Chisel Probe (MD6) Flat Probe (MT 1.5, MT 3.5), Diffuser Flat Probe (DF2). The disposable tip 42 can be selected for the specific type of surgery contemplated.

In an alternative embodiment, the laser fiber can be accompanied by an electrocautery conductor assembly 160 or only with an electrocautery conductor member. Although it is possible to provide an electrocautery capability by electrifying the disposable tip members, the preferred method is to include a separate, electrically isolated conductor tip members 150 connected by electrical cable 162 to the handle housing. Thus, the RG generator 170 transmits selected wave forms to the designated contact conductor tip 150 via cable 162 through the same passages used by the laser fiber from the lumen 140 to the outer tip end aperture 143. Quick disconnects are also used in the same manner as the laser fiber. If desired, both the disposable tip assembly 42 and shearing handle housing 44 can be provided with quick disconnects to allow laser energy and electrosurgical connection and transmission. Tips are also readily available from a number of commercial sources.

OPERATION OF THE SHEARS ASSEMBLY

Before the electrosurgical laser shear assembly 40 can be used, a disposable tip assembly 42 must be mounted in the shears housing 44. The surgeon selects the appropriate tip depending upon the type of surgery. A disposable tip assembly 42 is easily and quickly removed from the shear housing 44 by pivoting the locking rod 134 out of its biased position by pressing an arcuate release portion 148 defined by the rotator lock 96 so that the rotator lock member 96 rotates around the rotator lock pin 125 by compressing the lock spring and sliding the locking rod 134 out of both the bushing locking port 136 and the aligned activation plunger member oval lock port 120. The thumb loop member 92 is then pivoted away from the finger loop member 102 until the actuator plunger 100 member with the arcuate flanged slot 122 slides out of the distal end of the rotator member 84. In this position, the spatulated tip 80 can be removed from the flanged slot 122. The shears housing can then be sterilized and reused or covered with a protective sheath which can then be thrown away. Installing a new disposable tip is a simple process that is simply the reverse of the installation steps described hereinabove. The process begins by placing the spatulated tip 80 into the slot 122 and then pivoting the thumb loop member 92 back toward the finger loop 102 until the locking rod 134 snaps into place through the bushing locking port 136 and the aligned oval lock port 120. When this happens, the new spatulated tip 80 can be reciprocated by moving the actuation plunger member using the thumb loop 92. When the spatulated tip 80 is moved back and forth axially within the tubular shaft member 46, it moves the actuation link along with it. The translational motion of the actuation link rotates the inner cutter tip member 52 within the outer cutter tip bracket 50. The inner tip member 52 has a downward facing blade 75 which slices hard and soft tissue that is located between the blade edge and one side of the outer tip member. The contact tip member 150 is then energized with light energy or RF energy to perform additional cutting, ablation (vaporization) or coagulations. As previously noted a suction source (vacuum) 180 can be connected to a channel leading to the surgical site to remove excised or vaporized tissue.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

I claim:

1. A resposable surgical instrument with a disposable articulated tip assembly provided with a laser energy tip comprising:
    a disposable tip assembly which includes a mechanical cutting function and a laser function comprising an elongated housing defining a channel therein and having at a distal end a pivotal mounting for at least one jaw member;
    an elongated drive member positioned within said channel terminating substantially at its distal end with at least one linking means;
    at least one pivotal jaw member mounted to said elongated housing for rotation thereon interacting with a second jaw member to provide a tissue cutting mechanism and a laser tip mounted on one of said jaw members, a second channel defined in said elongated housing to receive an optical fiber connected to said laser tip and a light energy transmission connection mounted on an proximal end of said elongated housing to engage and transport light energy from a hand held detachable handle assembly, said handle assembly comprising a housing with an integral finger loop and a thumb loop member pivotally mounted to said handle housing, said handle housing defining a throughgoing bore which contains moveable linkage adapted to engage and move said disposable tip assembly,
    connection means secured to said handle housing for detachably mounting said disposable tip assembly, said handle housing defining a channel to hold an optic fiber transmission connection means to transmit light energy to said laser tip.

2. A resposable surgical instrument as claimed in claim 1 including a light energy generator source connected to said handle assembly and located remote from said handle assembly and wherein said laser tip has a cutting capability.

3. A resposable surgical instrument as claimed in claim 1 including a light energy generator source connected to said handle assembly and located remote from said handle assembly and wherein said laser tip has a coagulating function.

4. A reposable surgical instrument as claimed in claim 1 including a light energy generator source connected to said handle assembly and located remote from said handle assembly.

5. A reposable surgical instrument as claimed in claim 1 including a laser energy generator located remote from said handle assembly and selectively connected thereto to transmit light energy to said handle assembly.

6. A reposable surgical instrument as claimed in claim 1 including a suction source connected to said detachable handle assembly and adapted to communicate with a surgical site.

7. A combined mechanical cutter and laser function surgical instrument, comprising;
    a handle housing, a mechanical drive assembly mounted to said handle housing, a disposable tip assembly removably mounted to a connector of said handle housing, said disposable tip assembly comprising a hollow tube having a proximal and a distal end, a stationary jaw mounted to the distal end of said hollow tube, a movable jaw which pivots relative to said stationary jaw, actuating means coupled to said movable jaw for moving said movable jaw, said actuating means being driven from linkage in said handle housing mounted adjacent to said proximal end of said hollow tube, quick disconnect means mounted on the proximal end of said hollow tube to engage said connector of said handle housing, an optic fiber extending through said hollow tube and mounted to said stationary jaw engaging a laser energy dispensing tip member mounted to said stationary jaw, said dispensing tip member being connected to said optic fiber to receive energy carried by said optic fiber, and insulation mounted to said stationary jaw isolating said energy dispensing tip member from said stationary jaw.

8. A combined mechanical cutter and electrical function surgical instrument, comprising;
    a handle housing, a cutting tip assembly removably mounted to said handle housing, said cutting tip assembly comprising a hollow tube having a proximal and a distal end, a stationary jaw mounted to the distal end of said hollow tube, a movable jaw which pivots relative to said stationary jaw, actuating means coupled to said movable jaw for moving said movable jaw, said actuating means being driven from linkage in said handle housing mounted to said proximal end of said hollow tube, quick disconnect means mounted on the proximal end of said hollow tube to engage said handle housing allowing said cutting tip assembly to be selectively removed or connected to said handle housing, said quick disconnect means allowing transmission of mechanical energy and electrical energy from power sources to said cutting tip assembly, an insulated strand means capable of conducting electrical energy extending through said hollow tube and mounted to said stationary jaw, an electrical energy dispensing tip member mounted to said stationary jaw connected to said insulated strand means, and insulation means mounted to said stationary jaw insulating said energy dispensing tip member from said stationary jaw.

9. A combined function surgical instrument, comprising;

a handle housing, a disposable tip assembly removably mounted to said handle housing, said disposable tip assembly comprising a hollow tube having a proximal and a distal end, a stationary jaw mounted to the distal end of said hollow tube, a movable jaw which pivots relative to said stationary jaw, actuating means mounted in said tube coupled to said movable jaw for moving said movable jaw, said actuating means also being coupled at a proximal end of said hollow tube to a mechanical linkage which transmits motion from a driver assembly mounted in said handle housing, an energy conductive assembly extending through said hollow tube and mounted to said stationary jaw, an energy dispensing tip member mounted to said stationary jaw connected to said energy conductive assembly, insulation mounted to said stationary jaw isolating said energy dispensing tip member from said stationary jaw.

10. A combined function surgical instrument as claimed in claim 9 wherein said energy dispensing tip member is a laser conductive tip.

* * * * *